United States Patent
Kugimoto et al.

(10) Patent No.: US 8,530,645 B2
(45) Date of Patent: *Sep. 10, 2013

(54) METHOD FOR PRODUCING AMIDE COMPOUND

(75) Inventors: Junichi Kugimoto, Ube (JP); Tsunemi Sugimoto, Ube (JP)

(73) Assignee: Ube Industries, Ltd., Ube-shi, Yamaguchi (JP)

( * ) Notice: Subject to any disclaimer, the term of this patent is extended or adjusted under 35 U.S.C. 154(b) by 99 days.

This patent is subject to a terminal disclaimer.

(21) Appl. No.: 13/254,217

(22) PCT Filed: Mar. 4, 2010

(86) PCT No.: PCT/JP2010/053584
§ 371 (c)(1), (2), (4) Date: Sep. 1, 2011

(87) PCT Pub. No.: WO2010/101229
PCT Pub. Date: Sep. 10, 2010

(65) Prior Publication Data
US 2011/0313149 A1    Dec. 22, 2011

(30) Foreign Application Priority Data

Mar. 4, 2009  (JP) ................ 2009-049998
Apr. 13, 2009 (JP) ................ 2009-097168
Oct. 29, 2009 (JP) ................ 2009-248354

(51) Int. Cl.
*C07D 201/04*  (2006.01)
*C07D 225/02*  (2006.01)

(52) U.S. Cl.
USPC ........................................... 540/464

(58) Field of Classification Search
USPC ........................................... 540/464
See application file for complete search history.

(56) References Cited

U.S. PATENT DOCUMENTS

| | | | |
|---|---|---|---|
| 3,431,255 A | 3/1969 | Strauss et al. | |
| 3,825,532 A | 7/1974 | Kern et al. | |
| 5,145,998 A | 9/1992 | Sakito et al. | |
| 8,354,527 B2 * | 1/2013 | Kugimoto et al. | 540/464 |
| 2010/0029931 A1 | 2/2010 | Shibamoto et al. | |
| 2010/0029932 A1 | 2/2010 | Ishii et al. | |
| 2011/0092699 A1 | 4/2011 | Iwahama et al. | |

FOREIGN PATENT DOCUMENTS

| | | |
|---|---|---|
| DE | 25 34 538 A1 | 2/1976 |
| EP | 2 241 552 A1 | 10/2010 |
| GB | 1052284 | 12/1966 |
| GB | 1467565 | 3/1977 |
| JP | S46-23740 | 7/1971 |
| JP | H05-004964 | 1/1993 |
| JP | H9-301951 | 11/1997 |
| JP | H9-301952 | 11/1997 |
| JP | 2001-019670 | 1/2001 |
| JP | 2001-072658 | 3/2001 |
| JP | 2001-302602 | 10/2001 |
| JP | 2001-302603 | 10/2001 |
| JP | 2006-219470 | 8/2006 |
| WO | WO 2007-125002 A1 | 11/2007 |

OTHER PUBLICATIONS

International Search Report issued in International Application No. PCT/JP2010/053584, (2010).
K. Narasaka, et al., "Beckmann Rearrangement Catalyzed by the Combined Use of Tetrabutylammonium Perrhenate (VII) and Trifluoromethanesulfonic Acid," Chemistry Letter, The Chemical Society of Japan, No. 3, pp. 489-492(1993).
J. S. Sandhu, et al., "Indium trifuluoromethanesulfonate $(In(OTf)_3)$—A new catalyst for Beckmann rearrangement of ketoximes and facile dehydration of aldoximes," Indian Journal of Chemistry, vol. 41B, pp. 154-156, Jan. 2002.
J. S. Yadav et al., "$[Yb(OTf)3]$ catalyzed facile conversion of ketoximes to amides and lactams," Journal of Chemical Research, Synopsys Issue 5, pp. 236-238May 2002.
K. Ishihara, et. al., "Cyanuric Chloride as a Mild and Active Beckmann Rearrangement Catalyst," Journal of American Chemical Society, JACS Communications, vol. 127, No. 32, pp. 11240-11241, Jul. 2005.
M. Zhu, et al., "A mild and efficient catalyst for the Beckmann rearrangement, BOP-C1," Tetrahedron Letters, vol. 47, pp. 4861-4863 (2006).
Marin G. Hitzler, et al., "On the Reaction of Nitrilium Salts with Secondary Carboxamides," Liebigs Ann, pp. 247-257 (1996).
PCT Notification of Transmittal of English Language Translation of the International Preliminary Report on Patentability (Chapter I) mailed Sep. 22, 2011 including Written Opinion in International Application No. PCT/JP2010/053584.
English-language concise explanation of JP S46-023740 (1967).
Supplementary European Search Report issued in EP 10 74 8822, mailed Jul. 26, 2012.

* cited by examiner

*Primary Examiner* — Bruck Kifle
(74) *Attorney, Agent, or Firm* — Nixon Peabody LLP; Jeffrey L. Costellia

(57) ABSTRACT

This invention relates to a process for producing an amide compound by Beckmann rearrangement of an oxime compound using a compound having at least two electron-withdrawing leaving groups as a rearrangement catalyst, the process comprising a pre-preparation step in which the rearrangement catalyst and at least a part of the oxime compound are mixed and reacted; and a rearrangement reaction step in which the oxime compound is rearranged at a temperature higher than that in the pre-preparation step.

3 Claims, No Drawings

METHOD FOR PRODUCING AMIDE COMPOUND

TECHNICAL FIELD

The present invention relates to a process for producing an amide compound by Beckmann rearrangement of an oxime compound.

BACKGROUND ART

A common industrial process for producing an amide compound involves Beckmann rearrangement of a corresponding oxime compound, using concentrated sulfuric acid and oleum in an industrial scale. However, such strong acid must be used in stoichiometric amounts or more, which causes generation of a large amount of ammonium sulfate as a byproduct during neutralization. The process, therefore, requires facilities for producing concentrated sulfuric acid and oleum and for treating ammonium sulfate, which is a process with significant environmental burden and facility cost (Patent Document No. 1, Patent Document No. 2).

Recently, Beckmann rearrangement which does not require sulfuric acid or oleum in a large amount has been intensely investigated. There have been described processes utilizing as a catalyst a strong acid such as a mixture of an ammonium salt of rhenium peroxide and trifluoromethanesulfonic acid (Non-patent Reference No. 1), indium triflate (Non-patent Reference No. 2) or ytterbium triflate (Non-patent Reference No. 3). There have been further described processes utilizing a combination of an acid and a dehydrating agent, including a process where the rearrangement reaction is conducted using N,N-disubstituted amide compound as a solvent, phosphorus pentoxide or a condensed phosphoric compound and a non-fluorine containing sulfonic anhydride or sulfocarboxylic anhydride (Patent Document Nos. 3 and 4) and a process using a zeolite catalyst pretreated with an aqueous acid-containing solution (Patent Document No. 5). As a process without an acid, there have been described a process conducting the rearrangement reaction in the presence of a combination of a rhenium compound and a nitrogen-containing heterocyclic compound (Patent Document Nos. 6 and 7) and a process comprising using zinc oxide (Patent Document No. 8). Patent Document No. 9 describes a process where using cyanuric chloride (also known as trichlorotriazine) as a dehydrating agent in a carboxylic acid solvent, an oxime is reacted with a carboxylic acid to produce an ester, which is then rearranged. Patent Document No. 10 describes a process where a hydrochloride of an oxime is rearranged using, for example, cyanuric chloride (also known as trichlorotriazine) as an initiator. Although some processes using a catalyst such as those described above can give a high rearrangement yield, the processes employ a particular catalyst or solvent for which a recovering or recycling method has not been explicitly described and are thus imperfect as an industrial process.

Patent Document No. 11 describes a process in which an oxime compound undergoes Beckmann rearrangement in a polar solvent, using, as a rearrangement catalyst, an aromatic-ring containing compound, which (1) contains, as an aromatic-ring member, at least one carbon atom having a leaving group and (2) as aromatic-ring members, at least three heteroatoms and/or carbon atoms having an electron-withdrawing group and in which (3) two of the heteroatoms and/or the carbon atoms having an electron-withdrawing group are in ortho or para position to the carbon atom having a leaving group. Non-patent Document No. 4 also describes a similar approach.

Furthermore, Non-patent Document No. 5 has described that a phosphate having a heterocyclic structure similar to that of a catalyst described in Patent Document No. 11 is active as a catalyst for Beckmann rearrangement. Patent Document No. 12 has described that Beckmann rearrangement can be conducted in a nonpolar solvent, using a catalyst disclosed in Patent Document No. 11 and Non-patent Document No. 4. Patent Document Nos. 13 and 14 have described a process for Beckmann rearrangement of an oxime compound using a compound analogous to a catalyst disclosed in Patent Document No. 11.

Patent Document Nos. 15 and 16 describes Beckmann rearrangement of an oxime compound using thionyl chloride as a catalyst.

Among the catalysts for Beckmann rearrangement described in the above prior art documents, those that are relatively inexpensive and readily available as industrial chemicals include cyanuric chloride, phosphorous trichloride, phosphorous pentachloride, thionyl chloride and sulfuryl chloride. Among these, cyanuric chloride, phosphorous trichloride and phosphorous pentachloride are converted, when inactivated, into compounds insoluble in an organic solvent such as cyanuric acid and phosphoric acid, and therefore when being used in a large amount, they cause pipe blockage or poor heat transfer in an industrial process, and thus they are undesirable. Furthermore, phosphorous trichloride and phosphorous pentachloride are environmentally undesirable because of their severe toxicity.

In contrast, thionyl chloride is a catalyst suitable for industrial application because it is decomposed to give hydrogen chloride and sulfur dioxide without solid precipitation. Patent Document Nos. 15 and 16 disclose a process in which thionyl chloride and an oxime compound are mixed and heated, and it has been found that in the process, a yield varies depending on some factors such as a rate of temperature increase and a yield itself is low. Furthermore, Beckmann rearrangement is so exothermic that it cannot be controlled by the process described in Patent Document Nos. 15 and 16, which cannot be, therefore, applied to a larger industrial scale. There has been also found a problem that a desired amide compound cannot be produced with a high yield by the procedure in which thionyl chloride is added to a solution of an oxime compound heated to a predetermined temperature.

PATENT DOCUMENTS

Patent Document No. 1: Japanese Examined Patent Publication No. 1977-033118.
Patent Document No. 2: Japanese Laid-open Patent Publication No. 1993-4964.
Patent Document No. 3: Japanese Laid-open Patent Publication No. 2001-302602.
Patent Document No. 4: Japanese Laid-open Patent Publication No. 2001-302603.
Patent Document No. 5: Japanese Laid-open Patent Publication No. 2001-072658.
Patent Document No. 6: Japanese Laid-open Patent Publication No. 1997-301951.
Patent Document No. 7: Japanese Laid-open Patent Publication No. 1997-301952.
Patent Document No. 8: Japanese Laid-open Patent Publication No. 2001-019670.
Patent Document No. 9: Japanese Laid-open Patent Publication No. 1971-23740.

Patent Document No. 10: Japanese Laid-open Patent Publication No. 1972-18114.
Patent Document No. 11: Japanese Laid-open Patent Publication No. 2006-219470.
Patent Document No. 12: International Publication WO 07/125,002.
Patent Document No. 13: Japanese Laid-open Patent Publication No. 2008-156277.
Patent Document No. 14: Japanese Laid-open Patent Publication No. 2008-162935.
Patent Document No. 15: Japanese Laid-open Patent Publication No. 1976-041376.
Patent Document No. 16: Japanese Examined Patent Publication No. 1977-012198.
Patent Document No. 17: Japanese Laid-open Patent Publication No. 1987-215558.

NON-PATENT DOCUMENTS

Non-patent Document No. 1: K. Narasaka, et. al., Chemistry Letter, pp. 489-492 (1993).
Non-patent Document No. 2: J. S. Sandhu, et. al., Indian Journal of Chemistry, pp. 154-156 (2002).
Non-patent Document No. 3: J. S. Yadav, et. al., Journal of Chemical Research(S), pp. 236-238 (2002).
Non-patent Document No. 4: K. Ishihara, et. al., Journal of American Chemical Society, pp. 11240-11241 (2005).
Non-patent Document No. 5: M. Zhu, et. al., Tetrahedron Letters, pp. 4861-4863 (2006).
Non-patent Document No. 6: Marin G. Hitzler, et. al., Liebigs Ann, pp 247-257 (1996).

Problem to be Solved by the Invention

An objective of the present invention is to provide a process for producing an amide compound by Beckmann rearrangement of an oxime compound without generating ammonium sulfate as a byproduct, using a catalyst that is inexpensive and does not form precipitation when decomposed.

Another objective of the present invention is to provide an industrially suitable process for producing an amide compound by which a desired amide compound can be produced with a high yield using a small amount of a catalyst.

Means for Solving Problem

The present invention relates to the following items.

[1] A process for producing an amide compound by Beckmann rearrangement of an oxime compound using a compound having at least two electron-withdrawing leaving groups as a rearrangement catalyst, the process comprising a pre-preparation step in which the rearrangement catalyst and at least a part of the oxime compound are mixed and reacted; and a rearrangement reaction step in which the oxime compound is rearranged at a temperature higher than that in the pre-preparation step.

[2] The process as described in [1], wherein the pre-preparation step is conducted using a part of the oxime compound and in the rearrangement reaction step, the remaining oxime compound solution and the reactant in the pre-preparation step are mixed and subjected to a rearrangement reaction at a temperature higher than that in the pre-preparation step.

[3] The process as described in [1], wherein: in the pre-preparation step, the rearrangement catalyst and the whole amount of the oxime compound are mixed, and in the rearrangement reaction step, the mixture is heated.

[4] The process as described in any one of [1] to [3], wherein the rearrangement catalyst is at least one compound selected from the group consisting of thionyl chloride, cyanuric chloride, phosphorous trichloride and phosphorous pentachloride.

[5] The process as described in any one of [1] to [3], wherein the rearrangement catalyst is thionyl chloride.

[6] The process as described in [2], wherein the pre-preparation step is conducted using a part of the oxime compound and thionyl chloride, and a molar ratio of the oxime compound to thionyl chloride (oxime compound/thionyl chloride) is 0.5 or more.

[7] The process as described in any one of [1] to [6], wherein the rearrangement reaction step is conducted in the presence of a Lewis acid.

[8] The process as described in [7], wherein the Lewis acid is one or more halides of a metal selected from the group consisting of zinc, cobalt, antimony, tin and bismuth.

[9] The process as described in any one of [1] to [8], wherein the pre-preparation step is conducted at a temperature of 50° C. or lower and the rearrangement reaction step is conducted at a temperature of 60° C. to 160° C.

[10] The process as described in any one of [1] to [9], wherein the oxime compound is cyclododecanone oxime.

Effect of the Invention

The present invention allows a reaction to be completed by employing an inexpensive and industrially readily available rearrangement catalyst in a small amount in a process for producing an amide compound by Beckmann rearrangement of an oxime compound. The invention also allows an amide compound to be prepared in a high yield without generation of a byproduct such as ammonium sulfate or precipitation of catalyst decomposition products, thus resulting in an industrially suitable process.

In the Beckmann rearrangement reaction according to the present invention, no insolubles are formed, so that a reaction liquid is clear. In other words, no precipitates deposit in a reactor or pipe and thus blockage or poor heat transfer does not occur. Furthermore, although insolubles generally have a high boiling point, the system is free from such insolubles, so that a distillation tank bottom residue can be easily treated and a distillation loss is reduced. Furthermore, since insolubles are supposed to be inactivation products of a catalyst, the absence of insolubles is also a collateral evidence of high activity of the catalyst.

DESCRIPTION OF EMBODIMENTS

There will be detailed the present invention.
Oxime Compound

In the present invention, an oxime compound can be appropriately selected, without any particular restriction, depending on the targeted amide. For example, it may be the compound represented by formula (1).

wherein $R^1$ and $R^2$ represent an organic group respectively, or $R^1$ and $R^2$ together may represent a divalent organic group, whereby forming a ring with a carbon atom to which $R^1$ and $R^2$ attach.

Examples of an organic group for $R^1$ and $R^2$ include alkyl, alkenyl, alkynyl, cycloalkyl, cycloalkenyl, aryl, aralkyl, and aromatic or non-aromatic heterocycle.

Here, alkyl may be, for example, alkyl having 1 to 20, preferably 1 to 12, more preferably 2 to 8 carbon atoms. Specific examples include methyl, ethyl, propyl, isopropyl, butyl, isobutyl, s-butyl, t-butyl, pentyl, isopentyl, hexyl, isohexyl, heptyl, octyl, nonyl, decyl, dodecyl and pentadecyl.

Alkenyl may be, for example, alkenyl having 2 to 20, preferably 2 to 12, more preferably 2 to 8 carbon atoms. Specific examples include vinyl, allyl, 1-propenyl, 1-butenyl, 1-pentenyl and 1-octenyl.

Alkynyl may be, for example, alkynyl having 2 to 20, preferably 2 to 12, more preferably 2 to 8 carbon atoms. Specific examples include ethynyl and 1-propynyl.

Cycloalkyl may be, for example, cycloalkyl having 3 to 20, preferably 3 to 15 carbon atoms. Specific examples include cyclopropyl, cyclobutyl, cyclopentyl, cyclohexyl, cycloheptyl, cyclooctyl and cyclododecyl.

Cycloalkenyl may be, for example, cycloalkenyl having 3 to 20, preferably 3 to 15 carbon atoms. Specific examples include cyclopentenyl, cyclohexenyl and cyclooctenyl.

Examples of aryl include phenyl and naphthyl.

Examples of aralkyl include benzyl, 2-phenylethyl and 3-phenylpropyl.

Examples of aromatic or non-aromatic heterocycle include 2-pyridyl, 2-quinolyl, 2-furyl, 2-thienyl and 4-piperidinyl.

When $R^1$ and $R^2$ together represents a divalent organic group, they forms a ring with a carbon atom to which they attach. Examples of such a divalent organic group include straight-chain or branched alkylene groups, preferably straight alkylene groups, and examples of a ring formed include 3- to 30-membered rings, preferably 4- to 20-membered rings, more preferably 5- to 14-membered rings.

These organic groups, whether or not they form a ring, may have various substituents without any particular restriction as long as they do not inhibit the reaction. Examples of a substituent include halogen, oxo, mercapto, substituted oxy (alkoxy, aryloxy, acyloxy and so on), substituted thio, substituted oxycarbonyl, substituted or unsubstituted carbamoyl, cyano, nitro, substituted aminoalkyl, alkenyl, alkynyl, cycloalkyl, cycloalkenyl, aryl (phenyl, naphthyl and so on), aralkyl and heterocycle.

Specific examples of an oxime compound represented by Formula (1) include acetone oxime, 2-butanone oxime, 2-pentanone oxime, 3-pentanone oxime, 1-cyclohexyl-1-propanone oxime, benzaldehyde oxime, acetophenone oxime, benzophenone oxime and 4-hydroxyacetophenone oxime, and those forming a ring include cyclopropanone oxime, cyclobutanone oxime, cyclopentanone oxime, cyclohexanone oxime, cycloheptanone oxime, cyclooctanone oxime, cyclononanone oxime, cyclodecanone oxime, cyclododecanone oxime, cyclotridecanone oxime, cyclotetradecanone oxime, cyclopentadecanone cyclohexadecanone oxime, cyclooctadecanone oxime and cyclononadecanone oxime.

Oxime compounds may be selected and used alone or in combination of two or more.

An oxime compound is prepared by reacting a ketone corresponding to an oxime compound represented by Formula (1) with hydroxylamine. For example, cyclododecanone oxime can be prepared by reacting cyclododecanone and hydroxylamine generated by double decomposition of hydroxylamine sulfate, as described in Japanese Laid-open Patent Publication No. 2004-59553.

Furthermore, it may be also prepared by reacting a compound having a methyl or methylene group with a nitrite ester or nitrite salt in the presence of a compound prepared by introducing a protective group (for example, an acyl group such as acetyl) into an N-hydroxyimide compound derived from an aliphatic polycarboxylic anhydride (cyclic anhydride) or an aromatic polycarboxylic anhydride (cyclic anhydride) such as N-hydroxysuccinimide, N-hydroxyphthalic imide, N,N'-dihydroxypyromellitic N-hydroxyglutarimide, N-hydroxy-1,8-naphthalenedicarboxylic imide and N,N'-dihydroxy-1,8,4,5-naphthalenetetracarboxylic diimide and into a hydroxyl group in the N-hydroxyimide compound (for example, Japanese Laid-open Patent Publication No. 2009-298706).

Alternatively, it can be prepared by a method such as photo-nitrosation of a cycloalkane, or a reaction of a cycloalkanone with ammonia and hydrogen peroxide in the presence of a catalyst such as titanosilicate.

Rearrangement Catalyst

An example of a compound having at least two electron-withdrawing leaving groups of the present invention (hereinafter, referred to as "rearrangement catalyst") is a compound having at least two structures represented by formula (2):

$$A-X \qquad (2)$$

wherein A represents C (carbon atom), P, N, S, B or Si; X represents an electron-withdrawing leaving group; and A is attached to one or more atoms or groups in addition to X. A compound in which a plurality of Xs are attached to A is also included in the invention. When a plurality of A-Xs are present, these may be identical or different.

An electron-withdrawing leaving group in X may be a common elimination functional group such as halogen (fluorine, chlorine, bromine and iodine), —OR(R represents an organic group), carboxyl, amino and sulfonyloxy. Among these functional groups, halogen is preferable. Preferably examples of an organic group represented by R include, but not limited to, alkyl and haloalkyl.

Examples of alkyl for R include straight-chain or branched alkyl having 1 to 10 carbon atoms such as methyl, ethyl, propyl, isopropyl, butyl, isobutyl, s-butyl, t-butyl, pentyl and hexyl. Examples of haloalkyl for R include alkyl as described above having one or more halogen substituents such as fluorine, chlorine, bromine and iodine. Another example of a substituent is halogenated aryl.

There are no particular restrictions to a rearrangement catalyst as long as it is a compound having at least two structures represented by formula (2) in a molecule (including a compound in which a plurality of Xs are attached to A), and it may be a cyclic or acyclic compound.

Specific examples of a rearrangement catalyst in the present invention include phosphazene compounds (phosphazene derivatives), phosphine compounds (phosphine derivatives), imide compounds (imide derivatives), sulfonyl or sulfinyl compounds (sulfonyl or sulfinyl derivatives), silane compounds (silane derivatives), polyhalophosphates, cyclic compounds containing silicon as a ring member, phosphorous halides, halosulfuryls or any mixture of these.

Examples of a phosphazene compound include halophosphazene derivatives such as hexachlorophosphazene, hexafluorophosphazene and hexabromophosphazene.

Examples of a phosphine compound include dichloroethylphosphine, dichlorobutylphosphine and dichlorohexylphosphine.

Examples of an imide compound include cyanuric acid derivatives including cyanuric halide derivatives such as cyanuric chloride (also known as trichlorotriazine or cyanuric chloride acid, trichlorocyanuric acid) and sodium dichlorocyanurate; and hydantoin derivatives including halohydantoin derivatives such as 1,3-dichloro-5,5-dimethylhydantoin and 1,3-dibromo-5,5-dimethylhydantoin.

Examples of a sulfonyl or sulfinyl compound include trichloromethanesulfonyl chloride, trifluoromethanesulfonyl chloride and thionyl chloride.

Examples of a silane compound include halosilane derivatives such as dimethyldichlorosilane, chlorotriphenylsilane, dichlorodiphenylsilane and phenyltrichlorosilane.

Examples of a polyhalophosphate include methyldichlorophosphate and phenyldichlorophosphate.

Examples of a cyclic compound containing silicon as a member include silicon halonitrides.

Examples of a phosphorous halide include phosphorous trichloride and phosphorous pentachloride.

Examples of a halosulfuryl include sulfuryl chloride.

Among these, a compound having at least conjugated π electrons between structures (2) or a compound in which a plurality of Xs are attached to A is preferable, and trichlorocyanuric acid, thionyl chloride, phosphorous trichloride and phosphorous pentachloride can be more suitably used.

When a rearrangement catalyst (a compound having a structure represented by formula (2)) is a compound in which a leaving group X has —OR, the compound can be prepared before being used in the reaction. Alternatively, a corresponding compound having halogen as a leaving group X and an alcohol or metal alkoxide are combined in a reaction system for preparing an amide compound and in the reaction system, replacement of halogen with —OR can proceed to generate a compound having —OR as a leaving group X in the reaction system.

Pre-Preparation of an Oxime Compound and a Rearrangement Catalyst

An oxime compound and a rearrangement catalyst are blended at a temperature lower than that of Beckmann rearrangement of the oxime compound (hereinafter, referred to as "pre-preparation"). The pre-preparation step is conducted for forming a compound acting as a catalyst for Beckmann rearrangement (referred to as "active precursor"). Here, when a part of the oxime compound is used for pre-preparation, the oxime compound in the pre-preparation step and the oxime compound in the rearrangement reaction step are generally, but not necessarily, identical.

There will be detailed a reaction mechanism by which the above active precursor is formed in the pre-preparation step.

First, hydrogen in the oxime compound represented by formula (1) and a leaving group in the rearrangement catalyst are condensed and eliminated to give an oxime derivative represented by formula (3).

In formula (3), Y represents an electron-withdrawing substituent. For example, when cyanuric chloride is used as a catalyst, Y is 3,5-dichloro-2,4,6-triazinoxy group or 3-chloro-5-alkylidene-2,4,6-triazinoxy group (Formulae (4) and (5)). When the oxime compound is cyclododecanone oxime, the oxime derivative represented by formula (4) or (5) can be synthesized by the method disclosed in Japanese Laid-open Patent Publication No. 2009-185005 and can be quantified by HPLC.

When thionyl chloride is used as a rearrangement catalyst, the oxime derivative represented by formula (3) would be formed by the following mechanism. First, hydrogen chloride is eliminated from thionyl chloride and the oxime compound to form a compound having a structure represented by formula (6), and then intramolecular nucleophilic substitution of the compound represented by formula (6) gives a compound represented by formula (7). During this reaction, sulfur is eliminated as a form of sulfur dioxide. That is, when thionyl chloride is used as a rearrangement catalyst, Y would be chlorine. It is indicated by the fact that chlorine was detected in an about half amount of thionyl chloride fed while sulfur was detected in a small amount in ion chromatography analysis (using, for example, DIONEX-ICS1000 system from Mitsubishi Chemical Corporation) for an aqueous alkaline solution containing a gas which is generated by degassing a pre-preparation solution under a reduced pressure and, after removing gases generated from elimination and residual thionyl chloride, burning the solution by an automatic sample combustion device (for example, AQF-100 model from Mitsubishi Chemical Corporation) (described in Example B20).

High performance liquid chromatography analysis of a pre-preparation solution shows that, as an oxime compound as a starting material reduces, there emerge a plurality of new peaks which are different from an amide or lactam compound corresponding to the oxime compound; and after a polar solvent such as acetonitrile is added to the pre-preparation solution and then the solution is stored at room temperature for a whole day and night, these new peaks disappear and a peak of an amide or lactam compound of which peak volume corresponds to the amount of oxime compound reduction. This indicates that the amide or lactam compound is generated via an active intermediate containing one chlorine atom.

(3)

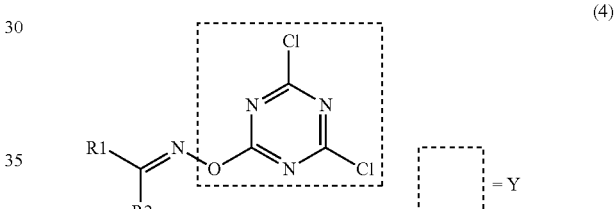

(4)

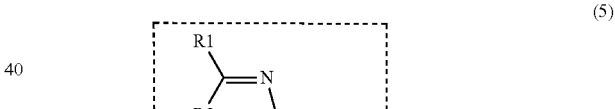

(5)

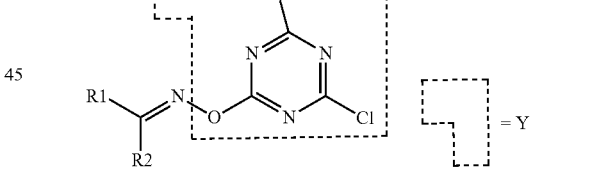

(6)

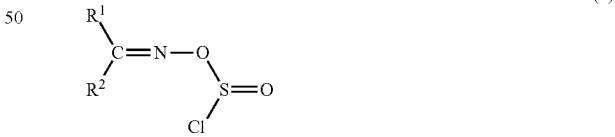

(7)

Here, as a rearrangement active intermediate, it is essential that an electron-withdrawing substituent remains in Y, and thus Y is electron-attractive. Therefore, bonding electrons between N and Y are drawn to the Y side while the nitrogen atom becomes electron-deficient, which initiates Beckmann rearrangement to form an amide or lactam intermediate represented by formula (8).

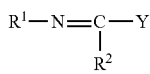
(8)

The amide or lactam intermediate represented by formula (8) reacts with an oxime compound to give an oxime-amide (or oxime-lactam) intermediate represented by formula (9) and also an amide-amide (or lactam-lactam) intermediate (represented by formula (10)) as a result of further Beckmann rearrangement.

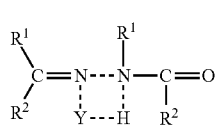
(9)

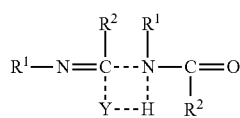
(10)

When an amide (or lactam) is eliminated from the oxime-amide (or oxime-lactam) intermediate (formula (9)), the oxime derivative represented by formula (3) is regenerated, and when an amide (or lactam) is eliminated from the amide-amide (or lactam-lactam) intermediate (formula (10)), the amide (or lactam) intermediate represented by formula (8) is regenerated, and thus a catalyst rearrangement cycle is completed.

The intermediates represented by formulas (3), (8), (9) and (10) are collectively referred to as "active precursor".

There will be described the reaction conditions in the pre-preparation step.

Blending Ratio in the Pre-Preparation Step

When a part of the oxime compound is used for the pre-preparation, a blending ratio of the oxime compound to the rearrangement catalyst ((oxime compound/rearrangement catalyst) molar ratio) depends on an oxime compound and a rearrangement catalyst selected; for example, when cyclododecanone oxime and thionyl chloride are selected as an oxime compound and a rearrangement catalyst, respectively, the ratio is 0.5 or more, preferably 0.5 or more and 10.0 or less, more preferably 1.0 or more and 5.0 or less, further preferably more than 1 and 5.0 or less, particularly preferably 1.5 or more and 3.0 or less.

A rearrangement catalyst is mixed in the pre-preparation in such a manner that the amount thereof becomes 0.01 mol % to 20 mol %, preferably 0.1 mol % to 5 mol % to the whole amount of the oxime compound used through the pre-preparation and the rearrangement steps.

If the amount of the oxime compound is too small, most of thionyl chloride as a rearrangement catalyst cannot be involved in forming a catalytically active species, and is thus ineffective for the pre-preparation.

An excessive amount of the oxime compound is undesirable because a pre-preparation apparatus becomes large. For example, when cyclododecanone oxime and thionyl chloride are used as an oxime compound and a rearrangement catalyst, respectively, cyclododecanone oxime has a higher melting point than a catalytically active species and is less soluble in a solvent described later at a temperature described later, and thus a large amount of the solvent must be used for preventing solid precipitation and blockage in the pre-preparation step, leading to disadvantageously large pre-preparation apparatus. Furthermore, an energy cost for recovery and recycling of the solvent disadvantageously increases. When a leaving group in a catalyst is completely eliminated to form an ether bond with the oxime compound (when the rearrangement catalyst is thionyl chloride, it is represented by formula (11), and when the catalyst is cyanuric chloride, it is represented by (12)), the moiety corresponding to Y (shown as a part surrounded by the broken line) is less electron-withdrawing and thus give insufficient positive charge to the nitrogen atom, so that Beckmann rearrangement is not initiated. For avoiding such inactivation, the oxime compound must not be excessive.

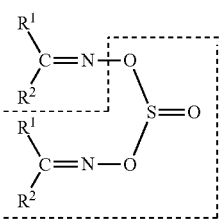
(11)

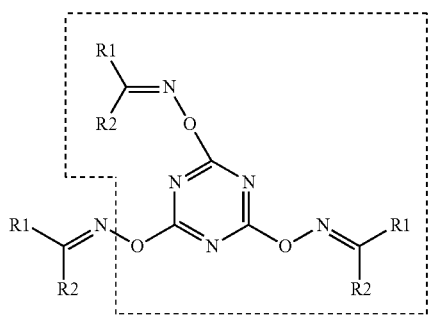
(12)

As described above, one objective of the pre-preparation step is to prevent excessive condensation reaction between a catalyst and an oxime compound and to efficiently prepare an active precursor.

Temperature of the Pre-Preparation Step

A temperature of the pre-preparation is, but not limited to, lower than that of Beckmann rearrangement described later, preferably 50° C. or lower, more preferably 30° C. or lower, most preferably room temperature or lower. A too high temperature of the pre-preparation is undesirable because most of a catalytically active species is converted into an amide or lactam compound while HY (for example, hydrogen chloride in case of thionyl chloride catalyst, and 2,4-dichloro-6-oxy-1,3,5-triazine in case of cyanuric chloride catalyst) is eliminated, leading to reduction in catalyst activity. There are no particular restrictions to a lower limit of a preparation temperature as long as a reaction system is not solidified at the temperature, but a temperature of 10° C. or lower, further of 0° C. or lower requires a cooling system, which is uneconomical.

Solvent in the Pre-Preparation Step

In the pre-preparation step of the present invention, a solvent can be used. Suitable solvents for each aspect are as follows.

When the pre-preparation is conducted using a rearrangement catalyst and at least a part of an oxime compound, there are no particular restrictions to a solvent used as long as it does not react with the rearrangement catalyst or the oxime compound. Examples of a solvent which can be used include organic acids such as acetic acid, propionic acid and trifluoroacetic acid; nitriles such as acetonitrile, propionitrile and benzonitrile; amides such as formamide, acetamide, dimethylformamide (DMF) and dimethylacetamide; aliphatic hydrocarbons such as hexane, heptane, octane and cyclododecane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; esters such as ethyl acetate and butyl acetate; fluorine-containing alcohols such as hexafluoroisopropyl alcohol and trifluoroethanol; and mixtures thereof.

When a leaving group X in a rearrangement catalyst is a halogen atom, a solvent other than water, alcohols, amines, mercaptans and amides can be used.

When thionyl chloride is used as a rearrangement catalyst, there are no particular restrictions to a solvent used in the pre-preparation as long as it does not react with thionyl chloride or an oxime compound. Examples of a solvent which can be used include nitriles such as acetonitrile, propionitrile and benzonitrile; aliphatic hydrocarbons such as hexane, heptane, octane and cyclododecane; aromatic hydrocarbons such as benzene, toluene and xylene; halogenated hydrocarbons such as chloroform, dichloromethane, dichloroethane, carbon tetrachloride, chlorobenzene and trifluoromethylbenzene; nitro compounds such as nitrobenzene, nitromethane and nitroethane; and mixtures thereof. Among these, since the use of aliphatic hydrocarbons or aromatic hydrocarbons allows a reaction rate of Beckmann rearrangement in the pre-preparation step to be easily controlled, they are particularly suitable solvents.

Unsuitable solvents include organic bases such as amines; those having an active hydroxyl group or analogous functional group such as water, alcohols and mercaptans; and those to which thionyl chloride acts as a chlorinating agent such as carboxylic acids and carboxylic acid esters.

The above solvents can be also used when thionyl chloride is used as a rearrangement catalyst and the rearrangement reaction step is conducted in the presence of a Lewis acid.

While there are no particular restrictions to the amount of a solvent in the pre-preparation step and it depends on a temperature and the size of a reactor, when cyclododecanone oxime and toluene are used as an oxime and a solvent, respectively, the solvent is used in such a manner that a weight concentration of the oxime is preferably 1% or more and 60% or less, particularly preferably 3% or more and 30% or less. A too small amount of a solvent is undesirable because the oxime compound is insufficiently dissolved, while an excessive amount of a solvent is also undesirable because recovery of the solvent requires additional work and increases energy cost.

Time of the Pre-Preparation Step

When a rearrangement catalyst and at least a part of an oxime compound are used for the pre-preparation, a time required for the pre-preparation varies depending on the type of the rearrangement catalyst used, a blending ratio of the oxime compound/the rearrangement catalyst, a preparation temperature, the amount of a solvent and the like, and is, but not limited to, preferably one minute or more and 24 hours or less, further preferably one minute or more and 10 hours or less.

A lower limit to a time required for the pre-preparation depends on a time required for generation of an active precursor and homogeneous blending of an oxime compound and a rearrangement catalyst. A too short time for the preparation is undesirable because outcomes such as a yield of an amide compound produced by Beckmann rearrangement are comparable with those in the case that a rearrangement catalyst is directly added to a rearrangement reactor. A too long time for the preparation is also undesirable because some of an active precursor is gradually converted into an inactive compound, which results in reduction in a rearrangement rate.

For example, when thionyl chloride is used as a rearrangement catalyst, cyclododecanone oxime is used as an oxime compound, a blending ratio is 1, a solvent is toluene, a preparation temperature is 25° C., and a concentration of cyclododecanone oxime in the pre-preparation is 3% by weight, the reaction time is suitably 1 minute or more and 10 hours or less, more preferably 1 minute or more and 3 hours or less, but when a blending ratio is more than 1, the time can be longer.

In terms of a blending ratio of an oxime compound and thionyl chloride and a reaction time in the pre-preparation, when a blending ratio of cyclododecanone oxime/thionyl chloride is 1/1 in Examples and Comparative Examples described later, five seconds of a pre-preparation time resulted in catalyst activity comparable with that in the case that thionyl chloride was directly added to a rearrangement reactor, and a conversion of cyclododecanone oxime after the rearrangement reaction was 48% (Comparative Example B5 described later). In contrast, when the time was 5 min, 10 min or 60 min, a conversion was as good as 100% (Examples B9, B8 and B10 described later), 99% for 2.5 hours (Example B11), 91% for 4.5 hours (Example B12), 77% for 15 hours (Comparative Example B1) and 68% for 24 hours (Comparative Example B2, which is higher activity than that in the case of direct addition to a rearrangement reactor).

When a blending ratio of cyclododecanone oxime/thionyl chloride is 2.5/1, a conversion of cyclododecanone oxime was 93% even after 24 hours (Example B14). When thionyl chloride was further increased by 20%, a conversion became 100% (Example B15).

While an upper limit to a time for the pre-preparation industrially depends on the size of a reactor, since a residence time of three hours or longer requires a larger apparatus, the time may be preferably less than three hours.

Apparatus Used in the Pre-Preparation

The pre-preparation in the present invention may be conducted using any of common mixing reactors including batch, semi-batch and continuous types. As long as a predetermined residence time is ensured, materials may be mixed in a pipe. Mixing method may be, in addition to a method using an agitator, in-line mixing using, for example, a static mixer.

Beckmann Rearrangement Reaction

There will be described a Beckmann rearrangement reaction.

The Amount of a Rearrangement Catalyst after the Pre-Preparation

In a Beckmann rearrangement reaction, when a part of an oxime compound is used in the pre-preparation step, the remaining oxime compound is added to conduct the rearrangement reaction. Here, assuming that the whole reactants after the pre-preparation are used, they are mixed in such a manner that the amount of the rearrangement catalyst is preferably 0.01 mol % to 20 mol %, more preferably 0.1 mol % to 5 mol % to the whole amount of the oxime compound used throughout the pre-preparation and the rearrangement reaction steps. A smaller amount of the rearrangement catalyst is undesirable because the rearrangement reaction is to be terminated. On the other hand, a too large amount of the rearrangement catalyst is also undesirable from an industrial standpoint because a catalyst cost increases and a cost for post-treatment and recycling of the catalyst increase.

Cocatalyst

In the present invention, an acid such as hydrogen chloride can be added as a cocatalyst to accelerate the rearrangement reaction. In particular, a Lewis acid is preferable because it can accelerate the rearrangement reaction without promoting hydrolysis of cyclododecanone oxime.

A Lewis acid can be one or more halides of a metal selected from the group consisting of zinc, cobalt, antimony, tin and bismuth; specific examples include zinc fluoride, zinc chloride, zinc bromide, cobalt fluoride, cobalt chloride, cobalt bromide, antimony penta fluoride, antimony pentachloride, antimony pentabromide, tin tetrafluoride, tin tetrachloride, tin tetrabromide, bismuth trifluoride, bismuth trichloride and bismuth tribromide. Zinc chloride and tin tetrachlorides are preferable, and zinc chloride is particularly preferable because it is significantly effective in acceleration of the reaction.

The amount of a cocatalyst is 0.01 to 10 molar equivalent, preferably 0.1 to 5 molar equivalent to the rearrangement catalyst. If the amount of the cocatalyst is too small, it is less effective in accelerating the rearrangement reaction. An excessive amount is undesirable from an industrial standpoint because the rearrangement reaction is not correspondingly accelerated and a cost for post-treatment and recycling the cocatalyst increases.

Solvent Used in Beckmann Rearrangement

It is preferable that a solvent used in the rearrangement reaction is identical to that in the pre-preparation because a production process can be simplified, but a different solvent can be used. When a different solvent is used, for example, a solvent can be replaced to a rearrangement solvent by adding the rearrangement solvent to a pre-preparation solution and then evaporating the pre-preparation solvent. Alternatively, Beckmann rearrangement can be conducted in a mixture of the pre-preparation solvent and the rearrangement solvent.

Temperature of Beckmann Rearrangement

A temperature of Beckmann rearrangement is 60 to 160° C., preferably 80 to 130° C. A too low reaction temperature is undesirable because a reaction rate is reduced and finally the reaction is to be terminated. Furthermore, at a low temperature, an oxime compound may be solidified or precipitated due to reduction in its solubility in a rearrangement solvent, which causes problems in operation. Increasing the amount of a solvent for avoiding the above problems is undesirable because problems such as increase in the amount of the solvent to be recovered and recycled arise and a production cost increases. A too high reaction temperature is also undesirable because the rearrangement reaction becomes so exothermic that a temperature rapidly increases and the reaction cannot be controlled. Furthermore, a too high reaction temperature results in a reduced rearrangement yield due to side reactions such as a condensation reaction and deterioration in product quality due to, for example, coloring.

Time of Beckmann Rearrangement

While a time of the rearrangement reaction depends on the types of an oxime compound and a rearrangement catalyst, a concentration of the catalyst and a reaction temperature, it is generally 5 min to 10 hours, preferably 10 min to 4 hours.

The reaction conditions are controlled such that the reaction can be easily controlled and an excessively larger reactor is not required.

Beckmann rearrangement reaction can be conducted under a reduced pressure, an ambient pressure or an increased pressure. It is not necessary to willingly conduct the reaction under an increased pressure, but the reaction can be conducted in a closed system to prevent a component which is generated from a rearrangement catalyst (for example, hydrogen halide when a leaving group X to be eliminated is a halogen atom) from being discharged outside the reaction system. Employing such a closed process can eliminate the necessity for separately installing a facility for adsorbing and eliminating a component such as hydrogen halide generated from a rearrangement catalyst. When hydrogen halide is generated, it is preferable since it is an acid in itself and promotes the rearrangement reaction as a cocatalyst.

An apparatus used in the rearrangement reaction can be a commonly used reactor such as a batch style reactor, a tubular continuous reactor and a stirred vessel type continuous reactor, and is suitably a multistage continuous stirred tank flow reactor in which a reaction temperature can be easily controlled and which can be easily operated.

After the rearrangement reaction, a product can be separated and purified by separating means such as filtration, concentration, distillation, extraction, crystallization, recrystallization, adsorption and column chromatography and a combination thereof.

For example, after the reaction of cyclododecanone oxime, the reaction can be worked up by adding water, extracting a product with an organic solvent and then evaporating the solvent to give laurolactam, which can be further separated and purified by, for example, distillation or crystallization.

There will be described the present invention with reference to Examples. The following examples are provided only for illustrating exemplary embodiments of the present invention and the present invention is not limited to these examples.

EXAMPLES

Reference Example 1

Production of Cyclododecanone Oxime

To a first pillow type oxime-forming reactor which has a liquid-phase volume of 30 L and inside of which was divided into four chambers each of which had an individual agitator, a 15% by weight aqueous solution of hyroxylamine sulfate (Wako Junyaku Inc.) at 1.5 kg/h and an oil phase supplied from a second oxime-forming reactor were fed A reaction temperature was set to 95° C., and a 25% by weight of aqueous ammonia solution was fed to each chamber at a rate of 32 g/h to initiate an oxime-forming reaction, to give an oil phase containing cyclododecanone oxime and toluene.

The aqueous phase was fed to the second oxime-forming reactor. The second oxime-forming reactor is a 15 L pillow type reactor inside of which was divided into four chambers. The aqueous phase of the oxime-forming reaction solution and a 25% by weight solution of cyclododecanone in toluene at a rate of 2 kg/h (equimolar to hydroxylamine sulfate fed to the first reactor) were fed to the reactor, and after a reaction temperature was set to 95° C., a 25% by weight aqueous ammonia solution was fed to each chamber at a rate of 16 g/h to initiate the oxime-forming reaction. The phases of the resultant reaction solution were separated and the oil phase was fed to the first oxime-forming reactor.

10 kg of the oil phase obtained in the first oxime-forming reactor was placed in a 20 L evaporator, and toluene was evaporated to provide 5.26 kg of a solution of cyclododecanone oxime in toluene. A content of cyclododecanone oxime was 50% by weight as determined by gas chromatography.

Reference Example 2

Drying of Cyclododecanone Oxime

The cyclododecanone oxime solution obtained in Reference Example 1 was evaporated by an evaporator to dryness for further removing toluene. The resultant powdery cyclododecanone oxime was placed in a vacuum oven and dried at 120° C. under a reduced pressure of 150 Pa for 24 hours, to give 2.62 kg of anhydrous cyclododecanone oxime.

Reference Example 3

Preparation of a Cyclododecanone Oxime Solution

Zinc chloride (18.2 g) was added to 5.26 kg of the 50% by weight solution of cyclododecanone oxime/toluene obtained in Reference Example 1, and dissolved by heating to 90° C. (referred to as, "50% by weight cyclododecanone oxime/zinc chloride solution"). Separately, the 50% by weight cyclododecanone oxime/toluene solution obtained in Reference Example 1 was diluted with toluene to prepare a 20% by weight cyclododecanone oxime/toluene solution and a 3% by weight cyclododecanone oxime/toluene solution. Here, the 20% by weight cyclododecanone oxime/toluene solution must be heated to 50° C. for avoiding precipitation of cyclododecanone oxime, whereas precipitation was not observed in the 3% by weight cyclododecanone oxime/toluene solution even at room temperature.

Examples A1 to A10 and Comparative Examples A1 to A3 are provided for showing relationship between reaction conditions and a conversion of cyclododecanone oxime and a yield of laurolactam when the pre-preparation was conducted by mixing and reacting a rearrangement catalyst and a part of cyclododecanone oxime compound and then Beckmann rearrangement was conducted at a temperature higher than that in the pre-preporation.

Example A1

Within a glove box, 0.033 g (0.17 mmol) of cyclododecanone oxime prepared in Reference Example 2 was dissolved in 0.400 g of a 5% by weight thionyl chloride (rearrangement catalyst)/toluene solution (0.020 g (0.17 mmol) as pure thionyl chloride), and the mixture was stirred using a magnetic stirrer at room temperature (25° C.) for 5 min, to conduct the pre-preparation of a rearrangement catalyst. After the pre-preparation, high performance liquid chromatography analysis indicated that cyclododecanone oxime had been consumed. Separately, within a glove box (under nitrogen atmosphere), in a flat-bottom flask equipped with a manifold, 3.285 g (16.64 mmol) of cyclododecanone oxime and 0.023 g (0.17 mmol) of zinc chloride were weighed and then 7.00 g of toluene was added, and the materials were dissolved by heating the mixture to 100° C. in an oil bath. To the zinc-chloride containing solution of cyclododecanone oxime in toluene, the reaction mixture which had been prepared in the pre-preparation using cyclododecanone oxime and thionyl chloride in 1:1 molar ratio was added, which then reacted for 60 min. The reaction solution was clear without turbidity, and gas chromatography analysis indicated that a conversion of cyclododecanone oxime was 100% and a laurolactam yield was 98.8%.

Example A2

The reaction was conducted as described in Example A1, except that the time of the pre-preparation of the rearrangement catalyst was 60 min. The reaction solution was clear without turbidity.

Example A3

The reaction was conducted as described in Example A1, except that 0.066 g of cyclododecanone oxime was used for the pre-preparation of the rearrangement catalyst and a molar ratio of cyclododecanone oxime to thionyl chloride (cyclododecanone oxime/thionyl chloride) was 2/1. The reaction solution was clear without turbidity.

Example A4

The reaction was conducted as described in Example A1, except that 0.166 g of cyclododecanone oxime was used in the catalyst pre-preparation and a molar ratio of cyclododecanone oxime to thionyl chloride was 5/1. Slight turbidity was observed in the reaction solution.

Example A5

The reaction was conducted as described in Example A1, except that 0.332 g of cyclododecanone oxime was used in the catalyst pre-preparation and a molar ratio of cyclododecanone oxime to thionyl chloride was 10/1. Turbidity was observed in the reaction solution.

Example A6

The reaction was conducted as described in Example A1, except that 0.022 g (0.11 mmol) of cyclododecanone oxime and 0.26 g of the 5% by weight thionyl chloride/toluene solution (0.013 g (0.11 mmol) as pure thionyl chloride) were used in the catalyst pre-preparation. The reaction solution was clear without turbidity.

Comparative Example A1

The reaction was conducted as described in Example A1, except that without conducting the pre-preparation of a rearrangement catalyst, a solution of thionyl chloride in toluene was directly added to a zinc-chloride containing solution of cyclododecanone oxime in toluene. Yellow-brown turbidity was observed in the reaction solution. Although a reaction time was increased to 120 min, a conversion of cyclododecanone oxime was unchanged. Yellow-brown turbidity was observed in the reaction liquid.

Comparative Example A2

The reaction was conducted as described in Example A1, except that the pre-preparation of a rearrangement catalyst was conducted at a temperature of 75° C. for 10 min. Yellow-brown turbidity was observed in the reaction liquid.

Example A7

To a 35 mL two-necked flat-bottom flask equipped with an overflow outlet, a 10% by weight solution of thionyl chloride (rearrangement catalyst) in toluene was fed at a rate of 26.2 g/h and a 3% by weight solution of cyclododecanone oxime in toluene was fed at a rate of 217.5 g/h, and the mixture was stirred at room temperature (25° C.) by a stirring bar to conduct the pre-preparation of a rearrangement catalyst and was flowed down to a rearrangement reactor. A small amount of the pre-preparation solution was sampled and burnt using an automatic sample combustion device (AQF-100 model from Mitsubishi Chemical Corporation) and a generated gas was absorbed by an aqueous solution of sodium hydroxide and analyzed by ion chromatography (using DIONEX-ICS1000 system from Mitsubishi Chemical Corporation), which resulted in that 0.28% by weight of chlorine was contained.

To a rearrangement reactor, the 50% by weight cyclododecanone oxime/toluene solution prepared in Reference Example 1 containing 0.52% by weight of zinc chloride was fed at a rate of 580 g/h. The rearrangement reactor consisted of two 160 mL of CSTRs (Continuous Stirred Tank Flow Reactor), in which a heat medium temperature in a jacket was adjusted such that a solution temperature was to be 105° C. A reaction time (the total of average residence times in CSTR1 and 2) is 0.3 hours, and a continuous reaction was conducted by maintaining the conditions for 10 hours. The reaction solution was clear without turbidity.

trichlorotriazine solution was directly added to a zinc-chloride containing solution of cyclododecanone oxime in toluene.

Example A9

The reaction was conducted as described in Example A3, except that phosphorous pentachloride was used as a rearrangement catalyst and 0.700 g of a 5% by weight solution of phosphorous pentachloride in toluene (phosphorous pentachloride: 0.17 mmol) was used in the pre-preparation.

Example A10

The reaction was conducted as described in Example A3, except that phosphorous trichloride was used as a rearrangement catalyst and 0.462 g of a 5% by weight solution of phosphorous trichloride in toluene (phosphorous trichloride 0.17 mmol) was used in the pre-preparation.

Table 1 shows the reaction conditions and the results for Examples A1 to A10 and Comparative Examples A1 to A3 described above.

TABLE 1

Reaction conditions and the results

| | | Pre-preparation conditions | | | Rearrangement reaction conditions | | | | | |
| --- | --- | --- | --- | --- | --- | --- | --- | --- | --- | --- |
| Example | Catalyst | Ox12/ catalyst molar ratio | Temperature (° C.) | Time (min) | Catalyst/ Ox12 mol % | $ZnCl_2$/ Ox12 mol % | Temperature (° C.) | Time (min) | Ox12 conversion (%) | Lc12 yield (%) |
| Example A1 | $SOCl_2$ | 1.0 | 25 | 5 | 1.0 | 1.0 | 100 | 60 | 100.0 | 98.8 |
| Example A2 | $SOCl_2$ | 1.0 | 25 | 60 | 1.0 | 1.0 | 100 | 60 | 100.0 | 98.5 |
| Example A3 | $SOCl_2$ | 2.0 | 25 | 5 | 1.0 | 1.0 | 100 | 60 | 100.0 | 99.1 |
| Example A4 | $SOCl_2$ | 5.0 | 25 | 5 | 1.0 | 1.0 | 100 | 60 | 100.0 | 99.0 |
| Example A5 | $SOCl_2$ | 10.0 | 25 | 5 | 0.9 | 0.9 | 100 | 60 | 94.2 | 91.5 |
| Example A6 | $SOCl_2$ | 1.0 | 25 | 5 | 0.7 | 1.0 | 100 | 60 | 100.0 | 99.6 |
| Comparative Example A1 | $SOCl_2$ | — | — | — | 1.0 | 1.0 | 100 | 60 | 38.3 | 36.4 |
| Comparative Example A2 | $SOCl_2$ | 1.0 | 75 | 10 | 1.0 | 1.0 | 100 | 60 | 44.0 | 42.5 |
| Example A7 | $SOCl_2$ | 1.5 | 25 | 6.7 | 1.5 | 1.5 | 105 | 18 | 100.0 | 99.2 |
| Example A8 | TCT | 1.0 | 25 | 5 | 0.4 | 1.0 | 100 | 60 | 100.0 | 98.9 |
| Comparative Example A3 | TCT | — | — | — | 0.4 | 1.0 | 100 | 60 | 54.9 | 53.3 |
| Example A9 | $PCl_5$ | 2.0 | 25 | 5 | 1.0 | 1.0 | 100 | 60 | 100.0 | 96.9 |
| Example A10 | $PCl_3$ | 2.0 | 25 | 5 | 1.0 | 1.0 | 100 | 60 | 99.3 | 95.0 |

Ox12: cyclododecanone oxime, Lc12: laurolactam, TCT: trichlorotriazine
In Example A7, a pre-preparation time is a residence time in a pre-preparation reactor, and a rearrangement time is the total residence time of two tanks CSTRs 1 and 2.

Example A8

The reaction was conducted as described in Example A1, except that trichlorotriazine was used as a rearrangement catalyst, 0.224 g of a 5% by weight solution of trichlorotriazine in toluene (trichlorotriazine 0.06 mmol) and 0.012 g (0.06 mmol) of cyclododecanone oxime were used in the pre-preparation, and a flat-bottom flask equipped with a manifold was charged with 3.00 g (15.20 mmol) of cyclododecanone oxime and 0.021 g (0.15 mmol) of zinc chloride.

Comparative Example A3

The reaction was conducted as described in Example A8, except that without conducting the catalyst pre-preparation, a Next, Examples B1 to 26 and Comparative Examples B1 to 5 are provided for determining relationship between the reaction conditions of the pre-preparation and the rearrangement reaction steps and a conversion of cyclododecanone oxime and a yield of laurolactam when thionyl chloride is used as a rearrangement catalyst.

Furthermore, Examples B20 to 23 are provided for understanding a mechanism of a reaction of an oxime compound with a rearrangement catalyst in the pre-preparation step by analyzing chlorine and sulfur contained in a solution after the pre-preparation step.

Example B1

In a flat-bottom flask equipped with a jacket, 0.281 g (0.236 mmol) of a 10% by weight thionyl chloride/toluene solution was placed, which was then cooled to 10° C. and stirred by a stirring bar. To the solution, 0.582 g (0.590 mmol) of the 20% by weight cyclododecanone oxime/toluene solution obtained in Reference Example 3 was added at 50° C. and pre-preparation was conducted for 10 min (ratio of cyclododecanone oxime/thionyl chloride: 2.5 (mol/mol)). A temperature rose to reaction due to reaction heat, but immediately decreased to 10° C. Here, even after the temperature decrease, precipitation was not observed. Furthermore, high performance liquid chromatographic analysis indicated that cyclododecanone oxime had been consumed, but a corresponding laurolactam was formed in a small amount. Then, this pre-preparation solution was added to 6.0 g of a 50% cyclododecanone oxime/zinc chloride solution (cyclododecanone oxime: 14.147 mmol and zinc chloride: 0.151 mmol) which was heated to 105° C. (thionyl chloride/cyclododecanone oxime 1.50 mol %, zinc chloride/cyclododecanone oxime: 0.96 mol %), and the mixture was reacted at the same temperature for 20 min. The reaction solution was clear without turbidity.

Example B2

The reaction was conducted as described in Example B1, except that 0.277 g of a 10% by weight thionyl chloride/toluene solution and 0.344 g of 20% by weight cyclododecanone oxime/toluene solution (a ratio of cyclododecanone oxime/thionyl chloride: 1.5 (mol/mol)) were used. The reaction solution was clear without turbidity.

Example B3

The reaction was conducted as described in Example B1, except that 0.283 g of a 10% by weight thionyl chloride/toluene solution and 0.704 g of 20% by weight cyclododecanone oxime/toluene solution (a ratio of cyclododecanone oxime/thionyl chloride: 3.0 (mol/mol))(thionyl chloride/cyclododecanone oxime: 1.50 mol %, zinc chloride/cyclododecanone oxime: 0.96 mol %) were used. The reaction solution was clear without turbidity.

Example B4

The reaction was conducted as described in Example B1, except that 0.274 g of a 10% by weight thionyl chloride/toluene solution and 0.228 g of 20% by weight cyclododecanone oxime/toluene solution (a ratio of cyclododecanone oxime/thionyl chloride: 1.0 (mol/mol)) were used.

Example B5

The reaction was conducted as described in Example B1, except that 0.292 g of a 10% by weight thionyl chloride/toluene solution and 1.212 g of 20% by weight cyclododecanone oxime/toluene solution (a ratio of cyclododecanone oxime/thionyl chloride: 5.0 (mol/mol)) were used.

Example B6

The reaction was conducted as described in Example B1, except that 0.318 g of a 10% by weight thionyl chloride/toluene solution and 2.638 g of 20% by weight cyclododecanone oxime/toluene solution (a ratio of cyclododecanone oxime/thionyl chloride: 10 (mol/mol)) were used.

Example B7

The reaction was conducted as described in Example B1, except that 0.272 g of a 10% by weight thionyl chloride/toluene solution and 0.113 g of 20% by weight cyclododecanone oxime/toluene solution (a ratio of cyclododecanone oxime/thionyl chloride: 0.5 (mol/mol)) were used.

Example B8

The reaction was conducted as described in Example B4, except that a rearrangement reaction time was 60 min.

Example B9

The reaction was conducted as described in Example B8, except that a pre-preparation time was 5 min.

Example B10

The reaction was conducted as described in Example B8, except that a pre-preparation time was 60 min.

Example B11

The reaction was conducted as described in Example B8, except that a pre-preparation time was 2.5 hours.

Example B12

The reaction was conducted as described in Example B8, except that a pre-preparation time was 4.5 hours.

Comparative Example B1

The reaction was conducted as described in Example B8, except that a pre-preparation time was 15 hours.

Comparative Example B2

The reaction was conducted as described in Example B8, except that a pre-preparation time was 24 hours.

Example B13

The reaction was conducted as described in Example B1, except that 0.225 g (0.189 mmol) of a 10% by weight thionyl chloride/toluene solution and 0.466 g (0.472 mmol) of a 20% by weight cyclododecanone oxime/toluene solution were used in the pre-preparation and a rearrangement reaction time was 30 min.

Example B14

The reaction was conducted as described in Example B13, except that a rearrangement reaction time was 24 hours.

Example B15

The reaction was conducted as described in Example B14, except that the amounts of a 10% by weight thionyl chloride/toluene solution and a 20% by weight cyclododecanone oxime/toluene solution under the pre-preparation conditions were as described in Example B1 (a ratio of pre-preparation: cyclododecanone oxime/thionyl chloride: 2.5 (mol/mol); rearrangement reaction: thionyl chloride/cyclododecanone oxime: 1.50 mol %, zinc chloride/cyclododecanone oxime 1.00 mol %).

Comparative Example B3

The reaction was conducted as described in Example B1, except that without conducting the pre-preparation of a rearrangement catalyst, 0.270 g of a 10% by weight thionyl chloride/toluene solution was directly added to 6.0 g of a 50% cyclododecanone oxime/zinc chloride solution (thionyl chloride/cyclododecanone oxime: 1.50 mol %, zinc chloride/cyclododecanone oxime 1.00 mol %) and a reaction time was increased to 60 min. Red-brown turbidity was observed in the reaction solution, and a reaction time was further increased to 120 min but a conversion of cyclododecanone oxime was not improved.

Comparative Example B4

The reaction was conducted as described in Example B1, except that the pre-preparation was conducted at 80° C.

Comparative Example B5

The reaction was conducted as described in Example B8, except that a pre-preparation time was 5 sec.

Example B16

The 50% by weight solution of cyclododecanone oxime in toluene prepared in Reference Example 1 was diluted with toluene to give a 30% by weight solution of cyclododecanone oxime in toluene. To 803 g of the solution (cyclododecanone oxime 1.22 moles), 2.50 g of zinc chloride (zinc chloride: 0.018 moles) was added to prepare a solution, which was placed in a 2 L three-necked jacketed flask equipped with a stirrer, a reflux condenser and a thermometer and was heated to 92° C. by circulating a heat medium. Separately, 22 g of a 10% by weight solution of thionyl chloride in toluene (thionyl chloride: 0.018 moles) and 175 g of a 2.8% by weight solution of cyclododecanone oxime in toluene (cyclododecanone oxime: 0.025 moles) were mixed at room temperature for 10 min to conduct pre-preparation. The pre-preparation solution was fed to the 2 L jacketed three-necked flask at a rate of about 5 mL/min using a microfeeder, and after the feeding, the reaction was continued for additional 60 min. The highest temperature during the catalyst feeding was 95° C. and the reaction could be controlled without runaway. Analysis of the resultant reaction solution by gas chromatography indicated that a conversion of cyclododecanone oxime was 100% and a yield of laurolactam was 97.6%.

Comparative Example B6

A mixture was prepared as described in Example B16, except that the amounts of cyclododecanone oxime, thionyl chloride, zinc chloride and toluene were reduced to 1/10, and placed in a 0.5 L jacketed three-necked flask equipped with a stirrer, a reflux condenser and a thermometer, and heated by circulating a heat medium. After an internal temperature exceeds 80° C., the reaction vigorously proceeded and an internal temperature rose so rapidly that the reaction became uncontrolled. The thermometer indicated 130° C. and the solution rushed up to the upper part of the reflux tube. After reacting for 60 min, a brownish-red precipitate was observed in the reaction solution.

Example B17

To a 35 mL two-necked flat-bottom flask equipped with an overflow outlet, a 10% by weight solution of thionyl chloride (rearrangement catalyst) in toluene at a rate of 26.2 g/h and a 3% by weight solution of cyclododecanone oxime in toluene were fed at a rate of 217.5 g/h, and the mixture was stirred at room temperature (20° C.) by a stirring bar to conduct the pre-preparation of a rearrangement catalyst and was flowed down to a rearrangement reactor. To a rearrangement reactor, the 50% by weight cyclododecanone oxime/zinc chloride solution prepared in Reference Example 3 was fed at a rate of 580 g/h. The rearrangement reactor consisted of two 160 mL CSTRs (Continuous Stirred Tank Flow Reactor), in which a heat medium temperature in a jacket was adjusted such that a solution temperature was to be 105° C. The reaction was continuously conducted for 10 hours. The reaction solution was clear without turbidity.

Example B18

The reaction was conducted as described in Example B17, except that in the pre-preparation step, the 10% by weight thionyl chloride/toluene solution was fed at a rate of 27.15 g/h, the cyclododecanone oxime/toluene solution had a concentration of 20% by weight and was fed at a rate of 56.3 g/h (a ratio of cyclododecanone oxime/thionyl chloride: 2.5 (mol/mol)), and the 20% by weight cyclododecanone oxime/toluene solution heated to 50° C. was fed. A pre-preparation temperature was 35° C.

Example B19(1)

The reaction was conducted as described in Example B18, except that the cyclododecanone oxime/toluene solution fed to a pre-preparation tank had a concentration of 20% by weight and was fed at a rate of 67.7 g/h (a ratio of cyclododecanone oxime/thionyl chloride: 3.0 (mol/mol)). Although white insoluble was generated in the pre-preparation reactor, the reaction was fed as a suspension to a rearrangement reactor. Analysis of the product indicated that a conversion of cyclododecanone oxime was 100% and a yield of laurolactam was 99.2%. The white insoluble in the pre-preparation reactor was collected by filtration, washed and dried. The analysis of the resultant powder by a fluorescent X-ray method shows chlorine: 7.44% by weight and sulfur: 950 ppm by weight. Furthermore, the insoluble was dissolved in acetonitrile and analyzed by high performance liquid chromatography (column: TSK-GEL ODS-80TS from Tosoh Corporation, eluent: acetonitrile/water, buffer: phosphoric acid), which resulted in detection of two large and broad absorption peaks other than a small amount of laurolactam (3.5% by weight). When the same sample was re-analyzed after additional 40 hours, the broad absorption peaks disappeared and laurolactam significantly increased (substantially 100% by weight).

Example B19(2)

Furthermore, 63 mg of the above powder (chlorine: 0.13 mmol) was added to a solution of 3.00 g of cyclododecanone oxime (15.2 mmol), 21 mg of zinc chloride (0.15 mmol) and 7.00 g of toluene, and the reaction was conducted at 100° C. for 1 hour. Analysis of the product showed that a conversion of cyclododecanone oxime was 100%, a yield of laurolactam was 98.9%, and the insoluble material in toluene generated during the pre-preparation was also active as a catalyst for Beckmann rearrangement.

Mass spectrometry showed that a molecular weight was 376, and elemental analysis showed hydrogen: 10.3% by weight, carbon: 70.3% by weight and nitrogen: 6.2% by weight. It was, therefore, estimated that the insoluble mainly contained an active species corresponding to (9) or (10) described above (theoretical atomic ratio for (9) or (10); hydrogen: 10.4% by weight, carbon: 69.8% by weight, nitrogen: 6.8% by weight, chlorine: 8.6% by weight, oxygen: 4.4% by weight; molecular weight: 412.5 (containing HCl) or 376 (elimination of HCl)).

Example B20

The pre-preparation was conduced as described in Example B19, except that the amount of the cyclododecanone oxime/toluene solution fed to the pre-preparation reactor was 45.1 g/h and a temperature of the pre-preparation reactor was 50° C. (residence time: 24.3 min; a feeding ratio of cyclododecanone oxime/thionyl chloride: 2.0 (mol/mol)). After degassing under a reduced pressure, the resultant pre-preparation solution was burnt using an automatic sample combustion device (AQF-100 model from Mitsubishi Chemical Corporation) and a generated gas was absorbed by an aqueous solution of sodium hydroxide and analyzed by ion chromatography (using DIONEX-ICS1000 system from Mitsubishi Chemical Corporation), which shows that 1.12% by weight of chlorine and 0.29% by weight of sulfur were contained. These corresponded to 50.1% of chlorine and 28.4% of sulfur in thionyl chloride fed. Next, 0.65 g of this pre-preparation solution was added to 6.14 g of a 50% cyclododecanone oxime/zinc chloride solution (cyclododecanone oxime: 14.48 mmol, zinc chloride: 0.155 mmol) preheated to 105° C. (a ratio of thionyl chloride fed in the pre-preparation step/cyclododecanone oxime (mol/mol): 1.29, a ratio of chlorine analysis value/cyclododecanone oxime (gram atom/mol): 1.29), and the reaction was conducted for 20 min, and analysis of the product showed that a conversion of cyclododecanone oxime was 84.0% and a yield of laurolactam was 82.6%.

Example B21

The pre-preparation was conduced as described in Example B20, except that the amount of the cyclododecanone oxime/toluene solution fed to the pre-preparation reactor was 67.7 g/h (residence time: 18.4 min; a feeding ratio of cyclododecanone oxime/thionyl chloride: 3.0 (mol/mol)). Analysis for chlorine and sulfur as described in Example B20 showed chlorine: 0.99% by weight and sulfur: 0.026% by weight, which corresponded to 57.8% and 3.5% of chlorine and sulfur, respectively, in thionyl chloride fed. Next, 0.86 g of this pre-preparation solution was added to 6.00 g of a 50% cyclododecanone oxime/zinc chloride solution (cyclododecanone oxime: 14.147 mmol, zinc chloride: 0.151 mmol) preheated to 105° C. (a ratio of thionyl chloride fed in the pre-preparation step/cyclododecanone oxime (mol/mol): 1.30, a ratio of chlorine analysis value/cyclododecanone oxime (gram atom/mol): 1.50), and the reaction was conducted for 20 min, and analysis of the product showed that a conversion of cyclododecanone oxime was 99.7% and a yield of laurolactam was 98.6%.

Example B22

The pre-preparation was conduced as described in Example B20, except that the amount of the cyclododecanone oxime/toluene solution fed to the pre-preparation reactor was 112.8 g/h (residence time: 12.4 min; a feeding ratio of cyclododecanone oxime/thionyl chloride: 5.0 (mol/mol)). Analysis for chlorine and sulfur as described in Example B20 showed chlorine: 0.70% by weight and sulfur: 0.035% by weight, which corresponded to 60.5% and 6.6% of chlorine and sulfur, respectively, in thionyl chloride fed. Next, 1.30 g of this pre-preparation solution was added to 6.04 g of a 50% cyclododecanone oxime/zinc chloride solution (cyclododecanone oxime: 14.241 mmol, zinc chloride: 0.152 mmol) preheated to 105° C. (a ratio of thionyl chloride fed in the pre-preparation step/cyclododecanone oxime (mol/mol): 1.28, a ratio of chlorine analysis value/cyclododecanone oxime (gram atom/mol): 1.55), and the reaction was conducted for 20 min, and analysis of the product showed that a conversion of cyclododecanone oxime was 85.6% and a yield of laurolactam was 84.7%.

Example B23

The pre-preparation was conduced as described in Example B20, except that the amount of the cyclododecanone oxime/toluene solution fed to the pre-preparation reactor was 225.6 g/h (residence time: 6.8 min; a feeding ratio of cyclododecanone oxime/thionyl chloride: 10.0 (mol/mol)). Analysis for chlorine and sulfur as described in Example B20 showed chlorine: 0.39% by weight and sulfur: 0.031% by weight, which corresponded to 60.9% and 10.8% of chlorine and sulfur, respectively, in thionyl chloride fed. Next, 2.53 g of this pre-preparation solution was added to 6.01 g of a 50% cyclododecanone oxime/zinc chloride solution (cyclododecanone oxime 14.171 mmol, zinc chloride: 0.151 mmol) preheated to 105° C. (a ratio of thionyl chloride fed in the pre-preparation step/cyclododecanone oxime (mol/mol): 1.30, a ratio of chlorine analysis value/cyclododecanone oxime (gram atom/mol): 1.58), and the reaction was conducted for 20 min, and analysis of the product showed that a conversion of cyclododecanone oxime was 59.7% and a yield of laurolactam was 58.8%.

Example B24

The reaction was conducted as described in Example B18 except that a reaction temperature was 80° C. and four CSTRs were used. A conversion of cyclododecanone oxime for each reactor at an outlet was 40.0%, 63.2%, 84.9% and 99.8%, and a yield of laurolactam at the outlet of the final reactor was 99.1%.

Comparative Example B7

The reaction was conducted as described in Example B18 except that a pre-preparation temperature was 80° C. A conversion of cyclododecanone oxime was 35.1%, 55.1% and 70.4% at outlets of a first, a second and a third reactors, respectively, and 74.1% even at an outlet of a fourth reactor, and a yield was also as low as 69.6%.

The reaction conditions and the results described above for Examples B1 to B24 are shown in Table 2. Furthermore, for Examples B20 to B23, the results of analysis for chlorine and sulfur in a pre-preparation solution are shown in Table 3.

From the results of analysis of chlorine and sulfur in the pre-preparation solution for Examples B20 to B23, chlorine was detected in about 50 to 60% to the amount of thionyl chloride fed while sulfur was detected in a small amount. It is, therefore, estimated that in the reaction of an oxime compound with thionyl chloride in the above pre-preparation step, the electron-withdrawing substituent Y is chlorine rather than sulfur.

TABLE 2

Reaction conditions and results

| | Pre-preparation conditions | | | Rearrangement reaction conditions | | | | | |
|---|---|---|---|---|---|---|---|---|---|
| Example No. | Ox12/SOCl$_2$ molar ratio | Temp. (° C.) | Time (min) | SOCl$_2$/Ox12 mol % | ZnCl2/Ox12 mol % | Temp. (° C.) | Time (min) | Ox12 conversion (%) | Lc12 yield (%) |
| Example B1 | 2.5 | 25 | 10 | 1.50 | 0.96 | 105 | 20 | 100.0 | 99.4 |
| Example B2 | 1.5 | 25 | 10 | 1.50 | 0.98 | 105 | 20 | 100.0 | 98.9 |
| Example B3 | 3.0 | 25 | 10 | 1.50 | 0.96 | 105 | 20 | 100.0 | 99.0 |
| Example B4 | 1.0 | 25 | 10 | 1.50 | 0.99 | 105 | 20 | 97.8 | 95.8 |
| Example B5 | 5.0 | 25 | 10 | 1.50 | 0.93 | 105 | 20 | 91.5 | 87.8 |
| Example B6 | 10.0 | 25 | 10 | 1.50 | 0.85 | 105 | 20 | 81.8 | 79.3 |
| Example B7 | 0.5 | 25 | 10 | 1.50 | 0.99 | 105 | 20 | 85.9 | 83.5 |
| Example B8 | 1.0 | 25 | 10 | 1.50 | 0.99 | 105 | 60 | 100.0 | 97.8 |
| Example B9 | 1.0 | 25 | 5 | 1.50 | 0.99 | 105 | 60 | 100.0 | 98.0 |
| Example B10 | 1.0 | 25 | 60 | 1.50 | 0.99 | 105 | 60 | 100.0 | 97.5 |
| Example B11 | 1.0 | 25 | 150 | 1.50 | 0.99 | 105 | 60 | 99.1 | 96.6 |
| Example B12 | 1.0 | 25 | 270 | 1.50 | 0.99 | 105 | 60 | 91.3 | 88.9 |
| Comparative Example B1 | 1.0 | 25 | 900 | 1.50 | 0.99 | 105 | 60 | 77.4 | 75.5 |
| Comparative Example B2 | 1.0 | 25 | 1440 | 1.50 | 0.99 | 105 | 60 | 68.9 | 67.1 |
| Example B13 | 2.5 | 25 | 10 | 1.29 | 1.03 | 105 | 30 | 100.0 | 99.1 |
| Example B14 | 2.5 | 25 | 1440 | 1.29 | 1.03 | 105 | 30 | 93.0 | 92.1 |
| Example B15 | 2.5 | 25 | 1440 | 1.50 | 1.00 | 105 | 30 | 100.0 | 99.0 |
| Comparative Example B3 | — | — | — | 1.50 | 1.00 | 105 | 120 | 25.1 | 23.1 |
| Comparative Example B4 | 2.5 | 80 | 10 | 1.50 | 0.96 | 105 | 20 | 59.8 | 56.7 |
| Comparative Example B5 | 1.0 | 25 | 0.08 | 1.50 | 0.99 | 105 | 60 | 48.0 | 46.1 |
| Example B16 | 1.4 | 25 | 10 | 1.45 | 1.45 | 92 | 60 | 100.0 | 97.6 |
| Comparative Example B6 | — | — | — | 1.45 | 1.45 | Runaway | 60 | 86.0 | 77.4 |
| Example B17 | 1.5 | 25 | 6.7 | 1.50 | 0.98 | 105 | 24.6 | 100.0 | 99.2 |
| Example B18 | 2.5 | 35 | 25 | 1.50 | 0.96 | 105 | 30.7 | 100.0 | 99.3 |
| Example B19(1) | 3.0 | 35 | 22 | 1.50 | 0.96 | 105 | 30.2 | 100.0 | 99.2 |
| Example B19(2) | Precipitated powder was used | | | 1.00 | 1.00 | 100 | 60 | 100.0 | 98.9 |
| Example B20 | 2.0 | 50 | 24.3 | 1.29 | 0.98 | 105 | 20 | 84.0 | 82.6 |
| Example B21 | 3.0 | 50 | 18.4 | 1.30 | 0.96 | 105 | 20 | 99.7 | 98.6 |
| Example B22 | 5.0 | 50 | 12.4 | 1.28 | 0.94 | 105 | 20 | 85.6 | 84.7 |
| Example B23 | 10.0 | 50 | 6.8 | 1.30 | 0.87 | 105 | 20 | 59.7 | 58.8 |
| Example B24 | 2.5 | 35 | 25 | 1.50 | 0.96 | 80 | 61.4 | 99.8 | 99.1 |
| Comparative Example B7 | 2.5 | 80 | 25 | 1.50 | 0.96 | 80 | 61.4 | 74.1 | 69.6 |

Ox12: cyclododecanone oxime, Lc12: laurolactam
pre-preparation time: an average residence time in a pre-preparation reactor for Examples B17 to B24 and Comparative Example B7
rearrangement reaction time: an average residence time to the second CSTR for Examples B17 to B23 and a residence time to the fourth CSTR for Example B24 and Comparative Example B7
Example B19(1) and Example B19(2) indicate the results of a continuous experiment and of a batch experiment for determining precipitation activity, respectively.

TABLE 3

Analysis of chlorine and sulfur in the pre-preparation solution

| | Catalyst (mol, g atom)/Ox12 (mol) | | | |
|---|---|---|---|---|
| Example No. | Fed SOCl$_2$ mol % | Analysis Cl mol % | Analysis S mol % | ZnCl$_2$ mol % |
| Example B20 | 1.29 | 1.29 | 0.37 | 0.98 |
| Example B21 | 1.30 | 1.50 | 0.05 | 0.96 |
| Example B22 | 1.28 | 1.55 | 0.08 | 0.94 |
| Example B23 | 1.30 | 1.58 | 0.14 | 0.87 |

Next, Examples C1 to C8 and Comparative Examples C1 to C3 are provided for determining relationship between the reaction conditions and a conversion of cyclododecanone oxime and a yield of laurolactam in a process for producing an amide compound by Beckmann rearrangement of an oxime compound using thionyl chloride in the presence of a Lewis acid.

Example C1

To a toluene solution prepared by dissolving 0.0624 g of thionyl chloride (0.524 mmol) in 5.0 g of toluene, 0.2089 g of cyclododecanone oxime (1.059 mmol, 2.0 molar equivalents of thionyl chloride) prepared as described in Reference Example 2 was added, and the mixture was stirred by a magnetic stirrer at room temperature (25° C.) for 5 min, for pre-preparation of a rearrangement catalyst. Separately, in a glass reaction tube (volume: 30 mL), 2.0 g of cyclododecanone oxime (10.16 mmol) was placed under an ambient atmosphere, to which 0.0145 g of cobalt chloride (CoCl$_2$) (0.112 mmol, 1.10 mol % of cyclododecanone oxime) and 4.0 g of toluene (Wako Pure Chemical Industries, Ltd.) as a solvent were then added in a glove box under nitrogen-gas atmosphere, and the tube was sealed and removed from the glove box. The above reaction tube charged with cyclododecanone oxime was placed in an oil bath at 105° C., and after an internal temperature reached about 100° C., 1.04 g of the toluene solution in the pre-preparation of the rearrangement catalyst (containing as thionyl chloride in the amount of 1.01 mol % to cyclododecanone oxime added, 0.0410 g of cyclododecanone oxime) was injected into the reaction tube via a syringe. After one hour, the reaction tube was removed from the oil bath and allowed to be cooled. The reaction solution was diluted with toluene and then quantitatively analyzed for laurolactam generated, by high performance liquid chromatography (analysis conditions of high performance liquid chromatography; column: ODS-H80 from Jsphere, column temperature: 40° C., eluent acetonitrile/water (volume ratio: 55/45), flow rate: 1 mL/min, detection wavelength: 210 nm). The analysis results showed that a conversion of cyclododecanone oxime was 100% and a yield of laurolactam was 101.5%.

A yield of laurolactam was calculated according to the following equation by an absolute calibration curve method.

Yield of laurolactam (%)=100×(moles of laurolactam generated)/{(moles of cyclododecanone oxime charged)+(moles of cyclododecanone oxime in a catalyst-containing toluene solution)}

Example C2

The reaction was conducted as described in Example C1, except that the amount of thionyl chloride was 0.99 mol % to cyclododecanone oxime charged and that tin tetrachloride ($SnCl_4$) in the amount of 0.92 mol % to cyclododecanone oxime was used in place of cobalt chloride.

Example C3

The reaction was conducted as described in Example C1, except that the amount of thionyl chloride was 1.03 mol % to cyclododecanone oxime charged and that antimony pentachloride ($SbCl_5$) in the amount of 1.04 mol % to cyclododecanone oxime was used in place of cobalt chloride.

Example C4

The reaction was conducted as described in Example C1, except that the amount of thionyl chloride was 1.03 mol % to cyclododecanone oxime charged and that bismuth trichloride ($BiCl_3$) in the amount of 1.28 mol % to cyclododecanone oxime was used in place of cobalt chloride.

Example C5

The reaction was conducted as described in Example C1, except that the amount of thionyl chloride was 1.02 mol % to cyclododecanone oxime charged and that zinc fluoride ($ZnF_2$) in the amount of 1.07 mol % to cyclododecanone oxime was used in place of cobalt chloride.

Example C6

The reaction was conducted as described in Example C1, except that the amount of thionyl chloride was 1.06 mol % to cyclododecanone oxime charged and that zinc chloride ($ZnCl_2$) in the amount of 1.05 mol % to cyclododecanone oxime was used in place of cobalt chloride.

Example C7

The reaction was conducted as described in Example C1, except that the amount of thionyl chloride was 1.03 mol % to cyclododecanone oxime charged and that zinc bromide ($ZnBr_2$) in the amount of 1.05 mol % to cyclododecanone oxime was used in place of cobalt chloride.

Example C8

In a glass reaction tube (volume: 30 mL), 2.0 g of cyclododecanone oxime (10.16 mmol) was placed under an ambient atmosphere, to which 0.0141 g of zinc chloride ($ZnCl_2$) (0.103 mmol, 1.01 mol % of cyclododecanone oxime), 0.36 g of a toluene solution containing 5.19% by weight of thionyl chloride (0.155 mmol as thionyl chloride, 1.53 mol % of cyclododecanone oxime) and 4.7 g of toluene were added at room temperature in a glove box under nitrogen-gas atmosphere, and the tube was sealed and removed from the glove box. The reaction tube was placed in an oil bath at 105° C. to initiate the reaction.

After one hour, the reaction tube was removed from the oil bath and allowed to be cooled. The reaction solution was diluted with toluene and then quantitatively analyzed for laurolactam generated, by high performance liquid chromatography. A conversion of cyclododecanone oxime was 100% and a yield of laurolactam was 100.5%.

Comparative Example C1

The reaction was conducted as described in Example C1, except that the amount of thionyl chloride was 1.04 mol % to cyclododecanone oxime charged and that zinc acetate ($Zn(OAc)_2$) in the amount of 1.43 mol % to cyclododecanone oxime was used in place of cobalt chloride.

Comparative Example C2

The reaction was conducted as described in Example C1, except that the amount of thionyl chloride was 1.01 mol % to cyclododecanone oxime charged and a Lewis acid was absent.

Comparative Example C3

The reaction was conducted as described in Example C8, except that after the materials other than thionyl chloride were placed as described in Example C8, the reaction tube was placed in an oil bath at 105° C. and after an internal temperature reached 99° C., 0.26 g of a toluene solution containing 7.21% by weight of thionyl chloride (0.160 mmol as thionyl chloride, 1.57 mol % of cyclododecanone oxime) was injected into the reaction tube via a syringe.

Table 4 shows the reaction conditions and the results in Examples C1 to C8 and Comparative Examples C1 to C3.

TABLE 4

| | Reaction conditions and results | | | | |
|---|---|---|---|---|---|
| Example No. | $SOCl_2$/Ox12 (mol %) | Lewis acid | Lewis acid/Ox12 (mol %) | Ox12 conversion (%) | Lc12 yield (%) |
| Example C1 | 1.01 | $CoCl_2$ | 1.10 | 100.0 | 101.5 |
| Example C2 | 0.99 | $SnCl_4$ | 0.92 | 100.0 | 101.2 |
| Example C3 | 1.03 | $SbCl_5$ | 1.04 | 100.0 | 100.5 |
| Example C4 | 1.03 | $BiCl_3$ | 1.28 | 100.0 | 100.7 |
| Example C5 | 1.02 | $ZnF_2$ | 1.07 | 100.0 | 102.5 |
| Example C6 | 1.06 | $ZnCl_2$ | 1.05 | 100.0 | 100.7 |
| Example C7 | 1.03 | $ZnBr_2$ | 1.05 | 89.4 | 88.7 |
| Example C8 | 1.53 | $ZnCl_2$ | 1.01 | 100.0 | 100.5 |
| Comparative | 1.04 | $Zn(OAc)_2$ | 1.43 | 5.6 | trace |

TABLE 4-continued

Reaction conditions and results

| Example No. | SOCl$_2$/Ox12 (mol %) | Lewis acid | Lewis acid/Ox12 (mol %) | Ox12 conversion (%) | Lc12 yield (%) |
|---|---|---|---|---|---|
| Example C1 Comparative Example C2 | 1.01 | — | — | 6.2 | amount 0.8 |
| Comparative Example C3 | 1.57 | ZnCl$_2$ | 1.01 | 68.0 | 67.9 |

Ox12: cyclododecanone oxime
Lc12: laurolactam

In Comparative Example C3, SOCl$_2$ was injected after an internal temperature of the reaction tube reached 99° C.

The invention claimed is:

1. A process for producing laurolactam by Beckmann rearrangement of cyclododecanone oxime using thionyl chloride as a rearrangement catalyst, the process comprising:

a pre-preparation step in which thionyl chloride and a part of cyclododecanone oxime are mixed, wherein a molar ratio of the cyclododecanone oxime to thionyl chloride (cyclododecanone oxime thionyl chloride) is 0.5 or more and 10.0 or less, and reacted at a temperature within a range that the reaction system is not solidified and 50° C. or less; and a rearrangement reaction step in which the remaining cyclododecanone oxime and the reactant in the pre-preparation step are mixed, and the cyclododecanone oxime is rearranged at 60° C. to 160° C.

2. The process according to claim 1, wherein the rearrangement reaction step is conducted in the presence of one or more a Lewis acids which is one or more halides of a metal selected from the group consisting of zinc, cobalt, antimony, tin and bismuth.

3. The process according to claim 2, wherein the Lewis acid is selected from the group consisting of cobalt chloride, tin tetrachloride, antimony pentachloride, bismuth trichloride, zinc fluoride, zinc chloride and zinc bromide.

* * * * *